United States Patent [19]
Collin

[11] Patent Number: 5,989,592
[45] Date of Patent: *Nov. 23, 1999

[54] INHIBITION OF COMPLEMENT PATHWAY BY SEA CUCUMBER FRACTIONS

[75] Inventor: Peter Donald Collin, Sunset, Me.

[73] Assignee: Coastside Bio Resources, Stonington, Me.

[ * ] Notice: This patent is subject to a terminal disclaimer.

[21] Appl. No.: 08/943,270

[22] Filed: Oct. 3, 1997

Related U.S. Application Data

[60] Provisional application No. 60/027,588, Oct. 3, 1996.

[51] Int. Cl.⁶ .......................... A61K 35/36; A61K 38/00; A61K 31/70; A61K 31/715
[52] U.S. Cl. .......................... 424/520; 424/572; 424/574; 514/2; 514/8; 514/21; 514/24; 514/25; 514/53; 514/54; 514/822; 514/885
[58] Field of Search ...................................... 424/520, 572, 424/574; 514/54, 24, 25, 42, 2, 53, 21, 8, 822, 885

[56] References Cited

PUBLICATIONS

Takada, Y. et al., Inhibition of the classical and alternative pathways by amino acids and their derivatives. *Immunology*, vol. 34, pp. 509–515 (1978).

Becker, E.L., The relationship of the structure of phosphonate esters to their ability to inhibit chymotrypsin, trypsin, acetylcholinesterase and C'ra. *Biochem. Biophys. Acta*, vol. 147, pp. 289–296 (1967).

Conrow, R.B. et al., Synthetic modulators of the complement system. 1. Synthesis and biological activity of 5,5',5"–[1,3,6–Naphthalenetriyltris(sulfonylimino)]–tris[1,3–benzenedisulfonic acid] hexasodium salt. *J. Med. Chem.*, vol. 23, pp. 240–242 (1980).

Hansch, C. et al., Structure–activity relationships in immunochemistry. 2. Inhibition of complement by benzamidines. *J. Med. Chem.*, vol. 17, pp. 1160–1167 (1974).

De Clercq, E. et al., Anti–complement activity of polynucleotides. *Biochem. Biophys. Res. Commun.*, vol. 67, pp. 255–263 (1975).

*Primary Examiner*—Michael G. Wityshyn
*Assistant Examiner*—Janet M. Kerr
*Attorney, Agent, or Firm*—Rothwell, Figg, Ernst & Kurz

[57] ABSTRACT

The present invention relates to methods for inhibiting the complement pathway in a mammal comprising administering an effective dose of a composition comprising an active ingredient selected from the group consisting of isolated sea cucumber (Phylum Echinodermata, Class Holothuroidea) body wall, isolated sea cucumber epithelial layer, isolated sea cucumber flower, sea cucumber fucosylated chondroitin sulfate, combinations thereof, active derivatives thereof or combinations of active derivatives thereof.

36 Claims, 4 Drawing Sheets

INHIBITION OF COMPLEMENT PATHWAY BY SEA CUCUMBER FRACTIONS

This application claims the benefit of U.S. provisional application No. 60/027,588, filed Oct. 3, 1996.

FIELD OF THE INVENTION

The present invention relates to compositions for inhibiting the complement pathway in warm-blooded animals. More particularly, the present invention relates to the inhibition of the complement pathway by administering distinct fractions of the echinoderm sea cucumber which comprise:

1. the isolated body wall of the sea cucumber, or its active derivatives,
2. the epithelial layer of the sea cucumber body wall, or its active derivatives,
3. the anterior flower or mouth portion of the sea cucumber, or its active derivatives,
4. sea cucumber fucosylated chondroitin sulfate, or
5. combinations thereof.

BACKGROUND OF THE INVENTION

The complement system is a group of proteins that constitutes about 10 percent of the globulins in the normal serum of humans (Hood, L.E. et al 1984, *Immunology*, 2nd Edition, The Benjamin/Cummings Publishing Co., Menlo Park, Calif. p. 339). Complement plays an important role in the mediation of immune and allergic reactions (Rapp, H. J. and Boros, T., 1970, *Molecular Basis of Complement Action*, Appleton-Century-Crofts Meredith, N.Y.). The complement system identifies foreign or damaged cells and tissue by covalently attaching a chemotactic protein (C3) which is recognized by host cell receptors. Complement is normally tightly regulated through the presence of complement inhibitors and the short half-life and substrate specificity of the enzymes involved in the activation cascade.

There are three major pathways of complement activation. First, the "classical pathway," which is activated by antibody/antigen binding. Second, the newly recognized "collecting pathway," activated by the binding of "mannose binding protein" to a complex carbohydrate, thereby activating a specific enzyme called "mannose binding protein activated serine proteinase" (MASP) that in turn activates another proteinase that generates chemotactic peptides such as C3. Third, the "alternative pathway," which is activated by the presence of a specific substrate called C3bB, a complex of complement proteins. The alternative pathway is controlled by the availability of the substrate C3bB. (Fearon & Austen, "Activation of the alternative complement pathway with rabbit erythrocytes by circumvention of the regulatory action of endogenous control proteins," *Journal of Experimental Medicine*, vol. 146, pp. 22–33 (1977); Pangburn, et al., "Localization of the heparin-binding site on complement factor H," *Journal of Biological Chemistry*, vol. 266, pp. 16847–53 (1991)).

The study of genetic deficiencies in different parts of the complement cascade have lead to an understanding of the roles of the complement system (reviewed in Figueroa & Densen, "Infectious diseases associated with complement deficiencies," Clinical *Microbiology Reviews*, vol. 4, pp. 359–95 (1991) and in Colten, "Complement deficiencies," *Annual Review of Immunology*, vol. 10, pp. 809–34 (1992)). Complement deficiencies or defects can lead to pyrogenic infections, glomerulitis, predisposition to autoimmune disease, infections with *Neisseria meningitides* and disseminated infections with *Neisseria gonorrhea*.

Some of the clinical implications of the release of one protein, C5a, of the complement pathway are as follows:
Rheumatoid Arthritis
Acute Gouty Arthritis
Acute Immunological Arthritis
Pulmonary Disorders
Adult Respiratory Distress Syndrome
Pulmonary Dysfunction-Hemodialysis
Chronic Progressive Pulmonary Dis-Cystic Fibrosis
Byssinosis
Asbestos-induced Inflammation
Inflammation of Systemic Lupus Erythematosus
Inflammation of Glomerulonephritis
Purtscher's Retinopathy
Hemorrhagic Pancreatitis
Renal Cortical Necrosis
Primary Biliary Cirrhosis Inflammation
Nephropathology
Cranial Nerve Damage in Meningitis
Tumor Cell Metastasis
Extended Tissue Destruction in Myocardial Infarction
Extended Tissue Destruction in Burns Many chemicals have been reported to diminish complement-mediated activity. Such compounds include: amino acids (Takada, Y. et al. *Immunology*,vol. 34, p. 509 (1978)); phosphonate esters (Becker, L. *Biochem. Biophy. Acta*, vol. 147, p. 289 (1967)); polyanionic substances (Conrow, R. B. et al *J. Med, Chem.*, vol. 23, p. 242 (1980)); sulfonyl fluorides (Hansch, C., Yoshimoto, M., *J. Med, Chem.*, vol. 17, p. 1160 (1974), and references cited therein); polynucleotides (De Clercq, P.F. et al. *Biochem. Biophys. Res. Commun.*, vol. 67, p. 255 (1975)). However, inhibitors of serine esterases, such as diisopropylfluorophosphate (DFP), were weak inhibitors and very toxic. It has been reported that the use of certain complement inhibitors to treat various inflammation states has desirable therapeutic effects. Buerke, et al., "Cardioprotective effects of a Cl esterase inhibitor in myocardial ischemia and reperfusion," *Circulation*, vol. 91, pp. 393–402 (1995); Testoni, et al., "Infusion of Cl-inhibitor plasma concentrate prevents hyperamylasemia induced by endoscopic sphincterotomy," *Gastrointestinal Endoscopy*, vol. 42, pp. 301–05 (1995); Moore, "Therapeutic regulation of the complement system in acute injury states," *Advances in Immunology*, vol. 56, pp. 267–99 (1994). There is therefor good evidence that complement inhibitors can functions as anti-inflammatory agents. Inhibition of complement activation can be measured as inhibition of overall complement activity (CH50). In terms of biological activity, inhibiting complement activation would decrease the inflammatory response because the anaphylatoxins (C3a, C3b, C4a and C5a) would not be produced.

Complement may also play a role in Alzheimer's disease. McGeer, et al., "Activation of the classical complement pathway in brain tissue of Alzheimer patients," *Neuroscience Letters*, vol. 107, pp. 341–6 (1989); Rogers, et al., "Complement activation by beta-amyloid in Alzheimer disease," *Proceedings of the National Academy of Science (USA)*, vol. 89, pp. 10016–20 (1992); Jiang, et al., "Beta-amyloid activates complement by binding to a specific region of the collagen-like domain of the Clq A chain," *Journal of Immunology*, vol. 152, pp. 5050–59 (1994), but this has not yet been investigated at the clinical level.

The only complement inhibitor currently available in any quantity is soluble CR1, a recombinant protein of 200kD.

CR1 is not a practical therapeutic compound, given both its size and the undesirable effect that chronic admistration would have on the beneficial functions of the complement pathway. Thus, there is a need for a non-toxic complement inhibitor which could be used therapeutically over a sustained time period.

Pharmaceutical companies are expanding efforts to screen and assay biologically active compounds from natural sources. The term that has been applied to this discovery process is "bio-prospecting." When bio-prospecting is successful in finding and identifying promising compounds, efforts are then made to determine and perfect the process by which the compound is produced in its active form. Useful processes develop from these bio-prospecting discoveries, as well as useful compositions of matter and methods of using the same.

The sea cucumbers constitute the taxonomic Class Holothuroidea in the Phylum Echinodermata. They possess an elongated body comprising a thick, leathery body wall of epithelial and collagenous layers surrounding the internal organs or viscera, an anterior mouth surrounded by numerous retractile tentacles (herein referred to as the "flower"), and a posterior portion comprising cloaca and anus. Muscle bands are found along the length of the interior surface of the body wall.

Sea cucumbers are a well-known Chinese delicacy harvested from many areas of the world and are a valuable trading resource in Chinese-speaking countries. There are a number of patent applications by Chinese groups relating to sea cucumbers as nutritional supplements (e.g., Chinese application CN 1065019) and patents or applications from Japanese groups relating to various carbohydrate moieties from sea cucumber as anticoagulants (JP 94070085 B2; WO 9008784) and as active components for treating AIDS (WO 9202231; WO 9009181). Historically, sea cucumbers for the worldwide market have been harvested, boiled with the muscles intact, and then salted and dried over an open flame. Salting and drying are the traditional methods of obtaining a product that is safe for storage and transportation. Nutritional supplements have been prepared by finely dividing these salted and fire-dried sea cucumber body walls for use in encapsulated products.

Sea cucumber tissue has been found to contain numerous compounds having potential as biologically active agents in medical and veterinary applications. These include sulfated polysaccharides (e.g. fucosylated chondroitin sulfate, Viera & Mourao, JBC, vol. 263, pp. 18176–83 (1988)), sterol glycosides, saponins (e.g., frondogenin and its glycosides, Findlay et al., J. Natural Products, vol. 47, pp. 320–324 (1984)), lactones (e.g., triterpenoid lactones, their acetates and glycosides, Findlay et al., supra), peptides, protamines, glycogens, saccharides (e.g. fucose, galactosamine, glucuronic acid, quinovose, xylose or O-methylglucose, Findlay et al., supra), polysaccharides (e.g., polyfucose sulfate, WO 9202231) and various amorphous compounds rich in saccharide moieties (Findlay et al., supra). Fucosylated chondroitin sulfate isolated from sea cucumber body walls by the methods of Viera & Mourao, supra, is especially interesting in that it demonstrates an anticoagulant activity unique to the family of chondroitin sulfate compounds that is apparently dependant on the particular spacial configuration of sulfate and fucose groups found in sea cucumber fucosylated chondroitin sulfates. Mourao, JBC, vol. 271(39)(27 Sept., 1996).

SUMMARY OF THE INVENTION

This invention provides a method for inhibiting the complement pathway in a warm-blooded animal in need of such treatment which comprises administering to said warm-blooded animal a therapeutically effective amount of a composition comprising the isolated body wall of a sea cucumber, the isolated epithelial layer of the body-wall of the sea cucumber, the flower of the sea cucumber, sea cucumber fucosylated chondroitin sulfate, their active derivatives or mixtures thereof.

BRIEF DESCRIPTION OF THE FIGURES

FIG. 3—Effect of sea cucumber fucosylated chondroitin sulfate (FCS) on complement factors C3a and C5a.

DETAILED DESCRIPTION OF THE INVENTION

Figure 1A:
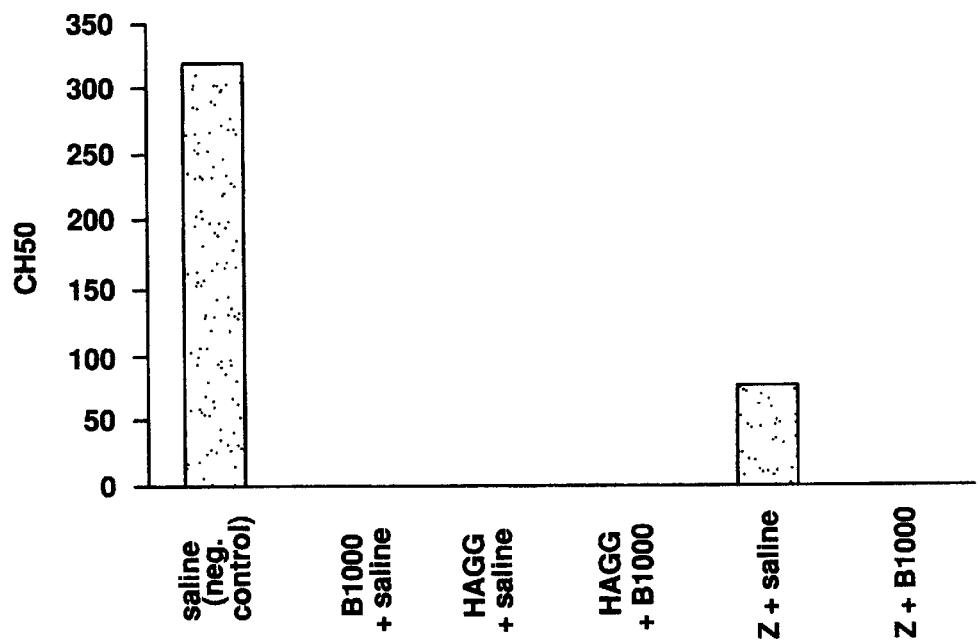
FIGS. 1 A–D—Graphs showing inhibition of classic complement pathway by B1000 according to four different parameters.

It has been found that fractions derived from the sea cucumber are active inhibitors of the complement pathway. This anticomplement property can be used in numerous applications in research and medicine in which complement is implicated, particularly those relating to inflammatory diseases such a rheumatoid arthritis or systemic lupus erythematosus (as stated above, inhibiting complement activation would decrease the inflammatory response because the anaphylatoxins (C3a, C3b, C4a and C5a) would not be produced) or to degenerative neurological conditions such as Alzheimer's disease and meningitis-induced cranial nerve damage. Complement has also been implicated in irritation caused by medical devices, such as adhesive bandages, stents or catheters. Coating these materials with the compounds of the present invention could ameliorate such irritation. Complement is also implicated in coronary reperfusion injury, and intervenous administration of the compounds of the present invention can be expected to ameliorate such injury.

As used herein, the term "sea cucumber" refers to any species of the Phylum Echinodermata, Class Holothuroidea, such as species of the genera Actinopyga (e.g., *A. lacanora, L. echinites*), Cucumaria (e.g., *C. frondosa, C. echinata, C. chronhjelmi*), Eupentacta (e.g., *E. quinquesemita*), Halodeima (e.g., *H. cinerascens*), Holothuria (e.g., *H. pervicax, H. atra, H. edulis, H. scabra, H. monoacaria, H. leucospilota*), Leptosynapta (e.g., *L. inhaerens*), Ludwigothuria (e.g., *L. grisea*), Microthele (e.g., *M. nobilis*), Molpadia (e.g., *M. musculus*), Parastichopus (e.g., *P. nigripunctatus*), Paracaudina (e.g., *P. chilensis*), Pelaaothuria, Pentacta (e.g, *P. australis*), Polycheira (e.g., *P. rufescens*), Psolus (e.a., *P. chitonoides*), Stichopus (e.g., *S. japonicus, S. chloronoyus, S. variegatus*), Synapta (e.g., *S. maculata*), Thelenota (e.g., *T. ananas*) or Thyone (e.g., *T. briareus*);

the term "flower" refers to the anterior portion of the sea cucumber comprising the mouth and retractile tentacles;

the term "B1000" refers to the isolated epithelial layer of the sea cucumber, substantially free of the flower portion, muscle, collagenous tissues and viscera;

the term "T2000" refers to the isolated flower portion of the sea cucumber, substantially free of other portions of the sea cucumber body;

the term "sea cucumber fucosylated chondroitin sulfate" refers to fucosylated chondroitin sulfate isolated from sea cucumber, or any compound having the structural and spacial configuration of sulfate and fucose groups essentially as found in fucosylated chondroitin sulfate isolated from sea cucumber;

the term "active derivative" refers to any compound, fraction or combination thereof, derived from a sea cucumber fraction described herein, that has inhibitory activity towards the complement pathway.

The sea cucumber fractions of the present invention may be in the form of powders, capsules, tablets solutions, suspensions, ointments, or any other means of delivery which those skilled in the medical and veterinary arts would deem appropriate. The formulation is dictated by the application, e.g., treatment of rheumatoid arthritis or burn conditions might call for a topical formulation for direct application to the affected area, while treatment of Alzheimer's disease or renal cortical necrosis would call for a systemically-dosed formulation such as an oral or injectable formulation. It is well with the skill of the medical or veterinary arts to determine a suitable formulation for any particular application. Furthermore, methods of making such formulations are well-known in the art (see, e.g. *Remington's Pharmaceutical Sciences*, 18th ed., Mack Publishing Co., Easton, Pa (1990)).

Active compositions that inhibit the complement pathway can be obtained from sea cucumber in a variety of ways. For example, sea cucumbers can first be cleaned of muscle bands and viscera, boiled (but preferably not salted), preferably for about ½ hour, and then dried, preferably in low-heat mechanical driers such as those employing "heat pump" technology. The dried tissue can further be ground or divided as needed for ultimate use. The preferred process whereby the tissue is not salted decreases the sodium content of the tissue and helps protect active ingredients from degradation. This fraction can be formulated and used directly as an anticomplement composition, either alone or in combination with other sea cucumber fractions, or used as a raw material for further purification of active derivatives, such as fucosylated chondroitin sulfate (Viera and Mourao, supra). A commercial sea cucumber body wall preparation is available from Coastside Bio Resources under the trademarks "Ginseng of the Sea™ T and SeaCuMAX™."

Another active fraction that is capable of inhibiting the complement pathway can be obtained from the flower portion of the sea cucumber. During the evisceration process described above, the anterior portion ("flower") of the sea cucumber is cut away from the viscera and body wall. The isolated flower is then heated in water, preferably for about ½ hour at a temperature preferably between about 140° F. and about –180° F., then dried at low temperatures (e.g. using conventional drying apparatus such as a heat pump and per se known techniques). This dried fraction, designated "T2000" by the inventor, can then be ground or divided as needed for formulation and used directly as an anticomplement composition, either alone or in combination with other sea cucumber fractions, or as a raw material for purification of active derivatives. The method and extent of division of the material is not critical to the invention, and can be readily determined by those skilled in the art according to the manner in which the composition will be used.

Still another active fraction that is capable of inhibiting the complement pathway can be obtained from the epithelial layer of the sea cucumber body wall. Muscle, viscera and flower are removed as described above, followed by isolation of the epithelial layer of the sea cucumber body wall from the harder collagenous layers beneath, preferably by one or more of the following means:

heating the body-wall in water at temperatures from about 140° F. to about 180° F., preferably at about 170° F., followed by mechanical separation by hand or machine (e,g., using machines known in the art as mincers or de-boners, which detect tissue density and separate harder tissues from softer tissues);

enzymatic hydrolytic separation, using, e.g., the organism's own digestive tract enzymes, proteases from mammalian sources, proteases from non-mammalian sources or acidic hydrolyses, preferably Alcalase (NOVO Nordisk Bio Chem, North Carolina), the enzyme preferably being in a solution of about 1% to about 10% enzyme, most preferably in a solution of about 10% enzyme;

scouring/scrubbing or de-boning processes known to those skilled in the potato or chicken processing arts.

Heating in water, followed by mechanical separation using a de-boner is most preferred. The epithelial fraction so obtained (designated "B1000" by the inventor) is a dark, moist, viscous, carbohydrate-rich matter. B1000 can be dried as described above, formulated and used directly as an anticomplement composition, either alone or in combination with other sea cucumber fractions, or used as a raw material for the purification of active derivatives.

An active derivative of sea cucumber body wall, fucosylated chondroitin sulfate, can be extracted from the tissues of any sea cucumber, whether dried, frozen or fresh, or from any extracted powder, liquid, hydrolysate, or suspension of sea cucumber tissue, preferably by methods set forth in Viera & Mourao, *JBC*, vol. 263, pp. 18176–83 (1988) (incorporated herein by reference). Extraction of fucosylated chondroitin sulfate from sea cucumber (or any other) tissue can also be achieved by ion disassociation, employing principles set forth in Eylers, *J. Exp. Biol.*, vol. 99, pp. 1–8 (1982). It has been found that treatment of polysaccharide-containing tissue with certain ions, such as $Na^+$or $K^+$leads to dissolution of the polypeptides, while treatment of the polypeptide solution with ions such as $Ca^{2+}$and $Mg^{2+}$leads to their precipitation. It has been found that it is necessary to maintain the pH of the preparation at or above about pH 6 during extraction in order to preserve optimal anticomplement activity. For example, acid hydrolysis, which leads to the loss of fucose and/or sulfate side-chains, has been found to essentially eliminate the anticomplement activity of sea cucumber fucosylated chondroitin sulfate.

The complement pathway inhibitor of the present invention may be administered orally, topically, rectally or via injection, alone or in mixture with an excipient or a carrier as set forth above and in accordance with the particular purpose of use. The active ingredient should be within a range of from about 0.01 to about 100 w/w %, or more preferably, of from about 0.05 to about 80 w/w %. The dose per day thereof, also depending upon the particular use to which the composition is put, the frequency of administrations, the form of medicament, the symptoms, age and body weight of the recipient of the composition, should be within a range of from about 0.1 to about 1,500 mg of the effective ingredient per kg of body weight, preferably from about 1 to about 1,000 mg/kg and most preferably about 25 mg/kg. The daily dosage of administration can be divided into two to four separate doses.

The following examples are intended to illustrate, but in no way to limit, the invention set forth in the claims.

EXAMPLE 1

Preparation of Whole Body Wall From Sea Cucumber

Muscle meat, viscera, anterior and posterior portions of the sea cucumber *Cucumaria frondosa* were removed in order to leave a sea cucumber body wall free of most, if not all of the above named portions. The thus obtained body wall was boiled for about ½ hour in fresh water and dried in a low heat utilizing a 40hp "heat-pump" dryer (Southwind Mfg., Nova Scotia, Canada). The body wall fraction was dried to about 3% moisture and finely divided.

EXAMPLE 2

Mechanical Extraction and Processing of Sea Cucumber Epithelium

A fraction termed B1000, consisting of sea cucumber epithelium, was produced by the following method. The anterior, posterior, viscera and muscles were removed from sea cucumbers of the species *Cucumaria frondosa* to obtain an isolated body wall. Body wall portions thus obtained were heated for about 30 minutes in fresh 170° F. water, then cooled on wire racks to room temperature. Next, the body wall portions were passed through an industrial machine known to those in the food processing arts as a de-boner or mincer (Paoli Machine, Ill.). The de-boner was adjusted to separate the softer outer epithelial layer from the harder collagenous portion of the body wall. The black viscous layer of the epithelium so separated, designated B1000 by the inventor, was dried by conventional means using a 40hp "heat pump" dryer as in Example 1 to approximately 3% moisture content and finely divided to obtain a powder.

EXAMPLE 3

Enzymatic Extraction and Processing of Sea Cucumber Epithelium

Enzymes were used to help separate the epithelial layer from the harder collagenous inner layer of body walls from sea cucumbers of the species Cucumaria frondosa. The body wall portions were isolated and heated in water as described in Examples 1 and 2. They were then soaked in a solution of 10% Alcalase (NOVO Nordisk Bio Chem, N.C.) in fresh water at a temperature of 130° F. (±30° F.). The time of soaking depended on the condition of the particular lot of body walls and their characteristics, and varied from about 15 min. to about 3 hours. The average time soaking in the enzyme solution was about one half hour. The body walls were then removed from the enzyme solution and processed by hand to further isolate the black epithelial layer B1000 from the underlying collagenous tissues. The B1000 thus obtained was dried and powdered as in Examples 1 & 2.

EXAMPLE 4

Extraction and Processing of Sea Cucumber Flower

A fraction termed T2000, derived from the sea cucumber flower, was obtained in the following manner.

During the processing operation of removing viscera and muscle set forth in Examples 1 and 2, the anterior portion of the sea cucumber *Cucumaria frondosa* was removed, taking care to include the mouth portion of the head with surrounding tentacles. This separated flower portion was then boiled for about ½ hour to obtain the fraction designated T2000 by the inventor. The T2000 was then dried in a conventional "heat-pump" dryer as in Examples 1–3 and finely divided.

EXAMPLE 5

Preparation of Derivative Fractions of B1000 and T2000

The finely divided powders of epithelial layer (B1000) and flower fraction (T2000) obtained in Examples 2 and 4, respectively, were further processed by mixing in an aqueous solution and rotating for 12 hours with a magnetic stirrer. The resultant solution was centrifuged at 30,000 RPM for one hour and the supernatant was removed and lyophilized.

EXAMPLE 6

Inhibition of Complement by a Derivative of B1000

Preparation of B1000 derivative: B1000 was pulverized with a mortar and pestle and put into a tube containing 0.15M NaCl at a weight to volume ratio of 100 $\mu$g/ml. The tube was rotated to mix at room temperature overnight and the following morning it was centrifuged to spin down the undissolved material. The supernatant was removed, and after final filtration through a 0.22 $\mu$m filter, the B1000 derivative was put into a sterile tube, capped tightly and stored at 40° C. The undissolved material was dried and weighted, and about half was found to have gone into solution.

Experiment with complement inhibition: Blood was collected from a healthy donor and allowed to clot at room temperature for 60 minutes. The serum was removed from the blood clot, and transferred to a clean tube. Preliminary studies indicated that when human serum was preincubated with 25 $\mu$g/ml B1000, half the available complement was inhibited (50% reduction in CH50 units).

Complement activators with known activities were prepared as positive controls. These included heat-aggregated gamma globulin (63° C., 30 minutes) and zymosan. The former (HAGG) is a potent activator of the classical pathway, and also activates the alternative pathway weakly. The latter (Z) consists of boiled and washed bakers' yeast and is a strong activator of the alternative pathway. HAGG was used at 14 mg/ml and Z at 10 mg/ml. These are relatively high doses. The B1000 extract was used straight.

The experiment was done by mixing 8 parts of the normal human serum (NHS) with 2 parts saline, saline plus activator (or B1000 extract), or activator plus B1000 extract. These mixtures were incubated for 30 minutes at 37° C. and the complement was examined by assaying total complement activity (CH50), C4d, Bb and iC3b split products. Results are shown in Table III.

TABLE I

| Incubation mixture | CH50 $\mu$g/ml | C4d $\mu$g/ml | Bb $\mu$g/ml | iC3b $\mu$g/ml |
| --- | --- | --- | --- | --- |
| NHS + saline (neg control) | 318 | 5.33 | 2.3 | 119.0 |
| NHS + HAGG + saline | 0 | 25.75 | 32.67 | 861.0 |
| NHS + Z + saline | 75 | 6.43 | 57.45 | 585.0 |
| NHS + B1000 + saline | 0 | 4.38 | 17.32 | 115.5 |
| NHS + HAGG + B1000 | 0 | 5.92 | 36.84 | 242.5 |
| NHS + Z + B1000 | 0 | 4.52 | 74.17 | 436.3 |

Figure 1B:
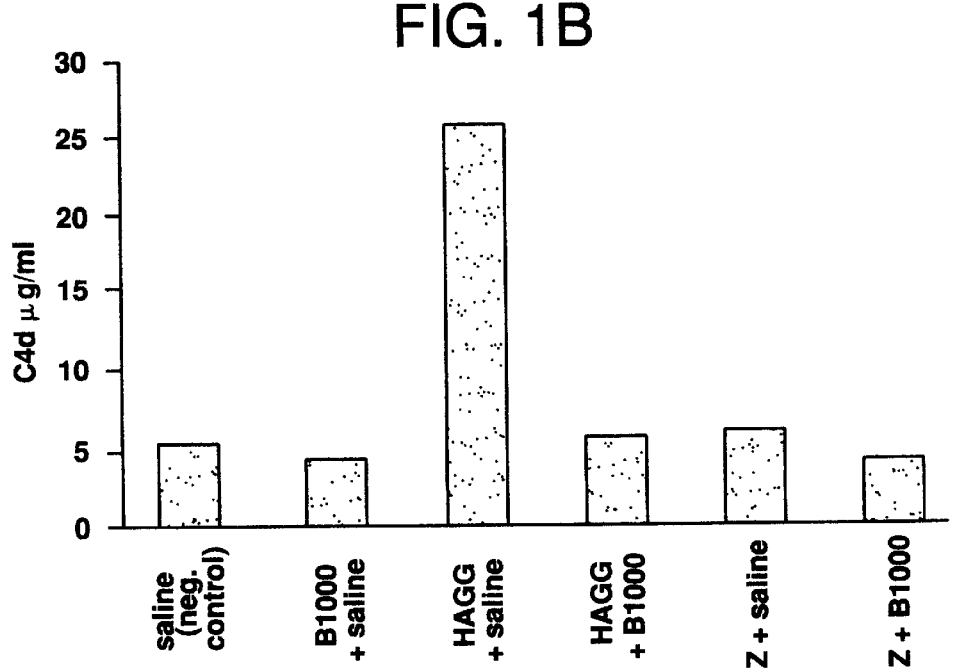
Figure 1C:
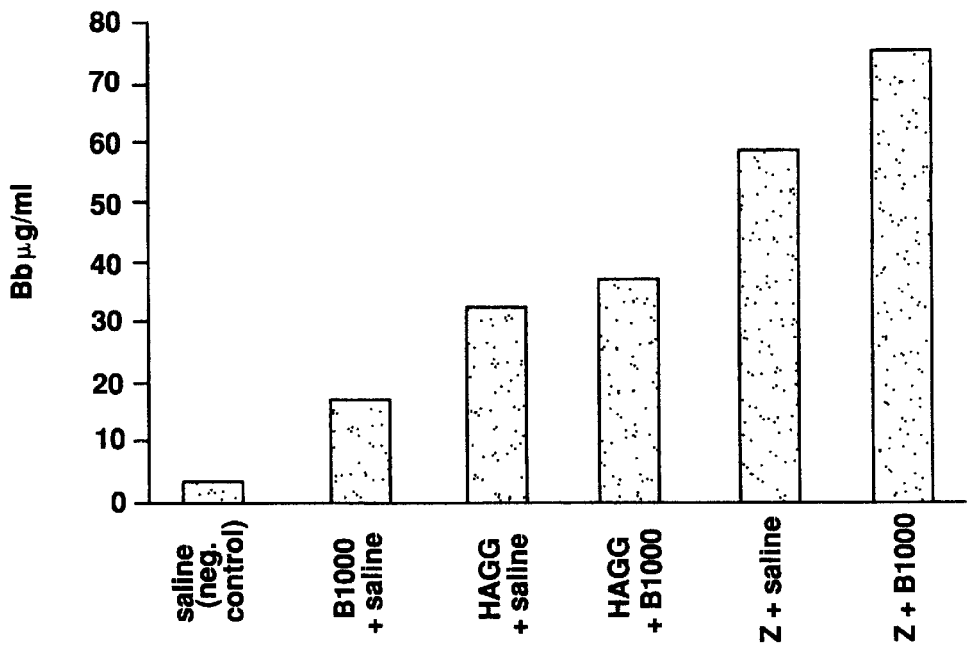
Figure 1D:
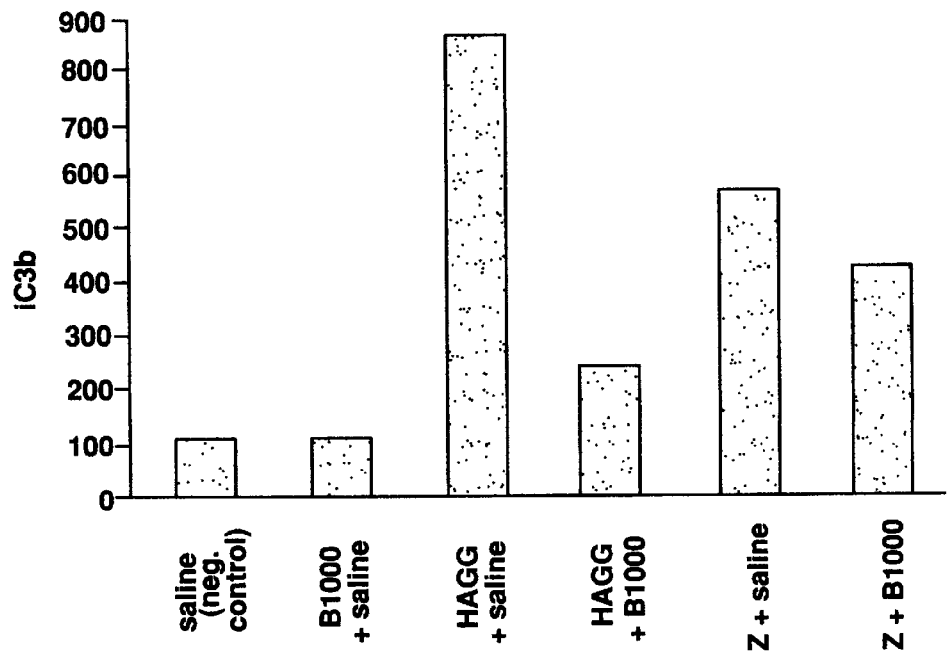

FIGS. 1A–D are graphic representations of the data of Table III. It can be seen in FIG. 1A that the B1000 by itself inhibited the classical pathway activation necessary for CH50 activity. In FIG. 1B, the C4d assay, the HAGG caused a good increase of C4d which it is supposed to do (classical pathway activation) but this increase in C4d was blocked by the B1000. In the Bb assay, there was some activation of the alternative pathway by B1000. There was no decrease in Bb produced by the HAGG or Z, and the increase seen was probably an additive effect of the B1000 activation by itself. In the iC3b assay, it appeared that the B1000 did nothing by itself and that it blocked most of the HAGG-mediated, and some of the Z-mediated iC3b production.

Figure 2:
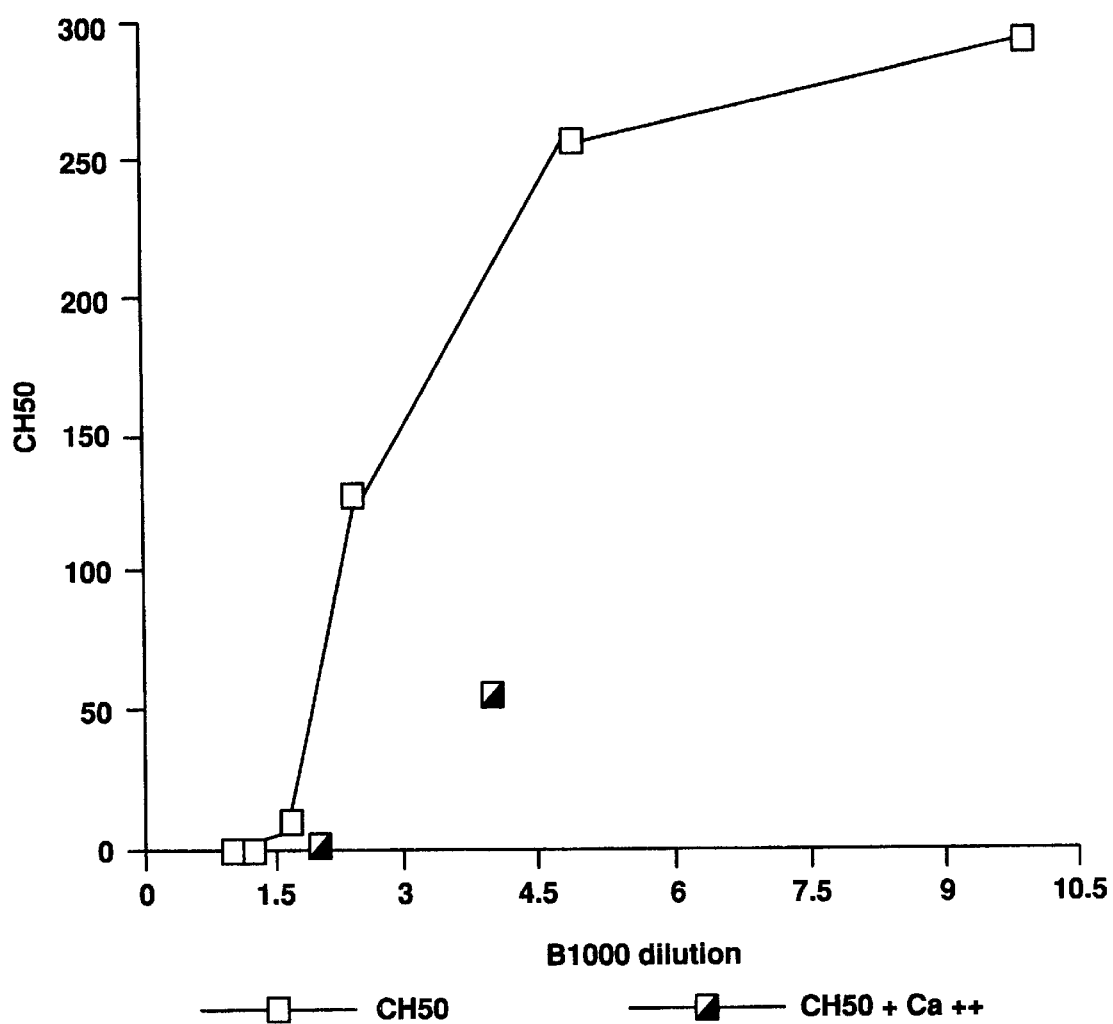
FIG. 2—Effect of B1000 on total complement activity (CH50).

Dose-response of B1000 effect on CH50: In order to find a dose of B1000 that didn't block 100% of the CH50 response (to determine when a slight change is happening in other assays) NHS (as above) was mixed with dilutions of B1000 made in saline. These were incubated at 37° C. for 30 minutes, and then the CH50 assay was done. Results are shown in FIG. 2.

EXAMPLE 7

Preparation of Fucosylated Chondroitin Sulfate From Sea Cucumber Body Wall

Fucosylated chondroitin sulfate was extracted from the body wall of the sea cucumber *Ludwigothurea grisea* by papain digestion, and purified by chromatography on DEAE-cellulose and Sepharose CL-4B.

The body wall of *L. grisea* was carefully separated from other tissues, immersed immediately in acetone and kept for 24 hours at 4° C. The dry tissue (50 g) was cut into small pieces, suspended in 1000 ml of 0.1M sodium acetate buffer (pH 6.0) containing 5 g of papain, 5 mM EDTA, and 5 mM cysteine, an incubated at 60° C. during 24 hours. The incubation mixture was then centrifuged (2000×g for 10 minutes at 10° C.), and the clear supernatant was precipitated with 2 volumes of 95% ethanol. After maintenance at −10° C. for 24 hours, the precipitate formed was collected by centrifugation (2000×g for 15 minutes at 10° C.), vacuum dried, dissolved in 50 ml of distilled water, exhaustively dialyzed against distilled water and lyophilized. About 5 g (dry weight) of crude extract was obtained after these procedures.

About 400 mg of the crude extract was applied to a DEAE-cellulose column (7×2 cm) equilibrated with 0.1 M sodium acetate buffer (pH 5.0) and washed with 100 ml of the same buffer. The column was developed by a linear gradient prepared by mixing 80 ml of 0.1M sodium acetate buffer (pH. 5.0) with 80 ml of 0.6M NaCl and 80 ml of 1.2M NaCl in the same buffer. The flow rate of the column was 12 ml per hour, and fractions of 3.0 ml were collected. They were checked by the Dubois et al. (*Analytical Chemistry*, vol. 28, pp. 350–354 (1956), incorporated herein by reference) and carbazole (Dische, *JBC* vol. 167, pp. 189–198, (1947), incorporated herein by reference) reactions, and conductivity was measured. Two main fractions of sulfated glycans (F1 and F2) were obtained, dialyzed against distilled water, and lyophilized.

About 40 mg of each fraction of sulfated glycans purified by DEAE-cellulose chromatography dissolved in 1.5 ml of 0.3M pyridine/acetate buffer (pH 5.0) was chromatographed on a Sepharose CL-4B column (115 cm×1.5 cm). Columns were eluted with the same buffer at a flow rate of 6 ml per hour and aliquots of approximately 1.5 ml were collected. The fractions were assayed by the Dubois et al. (supra) and carbazole (Dische, supra) reactions and by the metachromatic property (Albano and Mourao, *JBC* vol. 261, pp. 758–765 (1986), incorporated herein by reference). Columns were calibrated using blue dextran as a marker for $V_o$ and cresol red as a marker for $V_t$.

The fraction F-2 was found to comprise fucosylated chondroitin sulfate.

EXAMPLE 8

Inhibition of Complement By Fucosylated Chondroitin Sulfate

Blood was collected from a healthy donor and allowed to clot at room temperature for 60 minutes. The serum was removed from the blood clot, and transferred to a clean tube. The fucosylated chondroitin sulfate (FCS) of Example 10 was incubated in concentrations of 0.1 mg/ml, 0.4 mg/ml and 1 mg/ml for 30 minutes at 37° C. and the complement was examined by assaying total complement activity (CH50) as in Example 9. Complement inhibition was about 40% at 0.1 mg/ml fucosylated chondroitin sulfate, about 83% with 0.4 mg/ml and complete with 1.0 mg/ml. Assays using chondroitin sulfate derived from shark cartilage showed no complement inhibition (data not shown).

A second experiment to measure the complement factors C3a and C5a was carried out using heat-aggregated gamma globulin (63° C., 30 minutes)(HAGG),a complement activator with known activity was prepared as a positive control. HAGG is a potent activator of the classical pathway, and also activates the alternative pathway weakly. HAGG was used at 14 mg/ml, a relatively high dose.

Figure 3A:
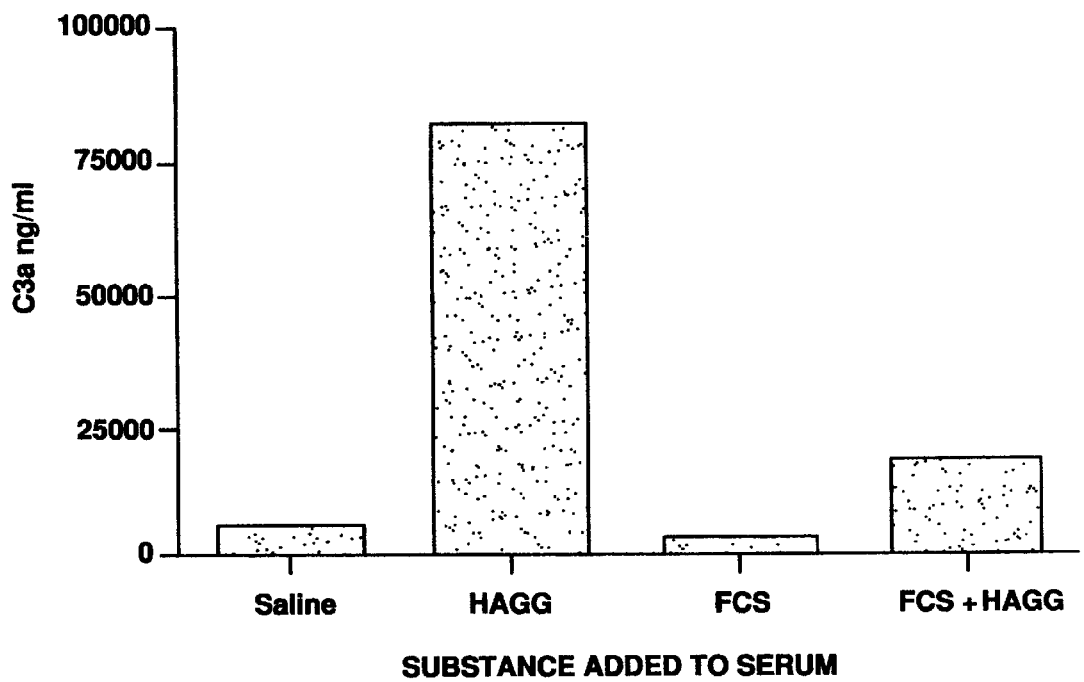
Figure 3B:
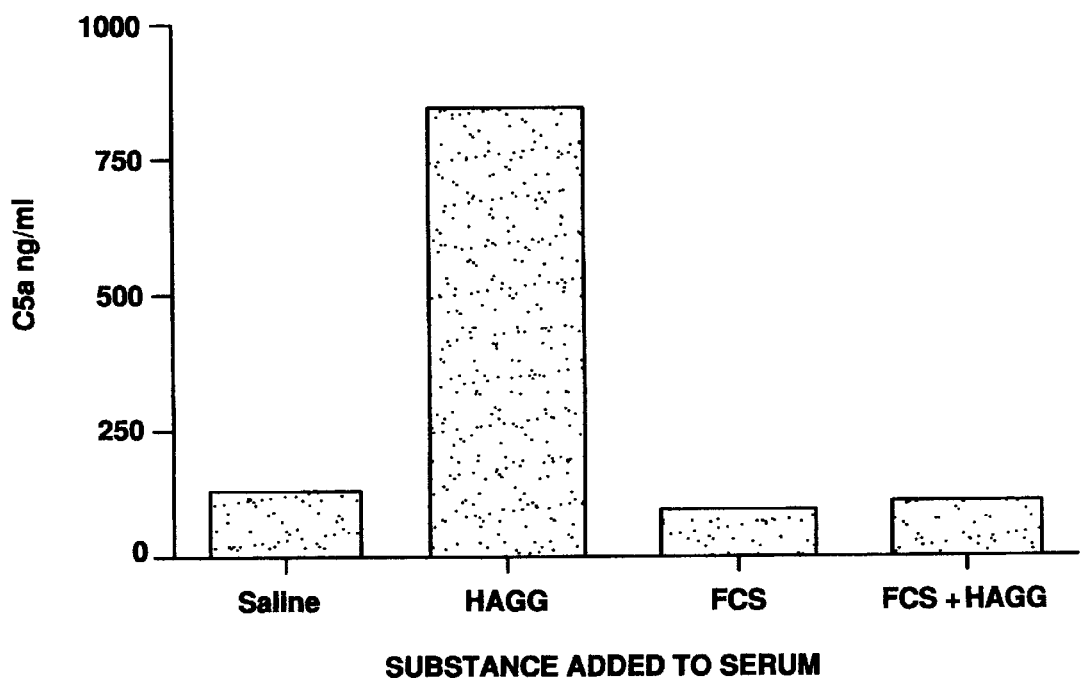

The experiment was done by mixing 8 parts of the normal human serum (NHS) with 2 parts saline, saline plus HAGG (or FCS), or HAGG plus FCS. These mixtures were incubated for 30 minutes at 37° C. and the complement was examined by assaying for levels of C3a and C5a. Results are shown in FIG. 3. As can be seen, fucosylated chondroitin sulfate has a strong inhibitory activity toward both C3a and C5a, both alone and with the classic complement pathway inhibitor HAGG.

EXAMPLE 9

Effect of Defucosylation on Anticomplement Activity

Fucosylated chondroitin sulfate obtained as in Example 7 was further processed by mild acid hydrolysis to remove the sulfated fucose side chains. Hydrolysis was performed under mild conditions by dissolving 50 mg of fucosylated chondroitin sulfate in 1.0 ml of 150 mM $H_2SO_4$, maintained at 1° C. for 30 minutes. The pH of the solution was adjusted to 7.0 with a 0.3 ml of ice-cold 1.0M NaOH. The release of sulfated fucose groups was identified by positive Dubois test (Dubois et al., *Analytical Chemistry*, vol. 28, p. 350–354 (1956)) and the absence of carbazole (Bitter, et al., *Analytical Biochemistry*, vol. 4, p. 330–334 (1962)).

The defucosylated chondroitin sulfate ("de-FCS") thus obtained was made up in a solution at 10 mg/ml in saline. Serum was obtained from blood drawn from a healthy adult volunteer. The serum was mixed with saline or the de-FCS, at a constant ratio of 9 parts serum and 1 part saline or de-FCS, and incubated for 30 minutes at 37° C. to determine its effect on complement activation. The results are shown in Table II, below.

TABLE II

| Sample | CH50 µg/ml | Bb µg/ml | C4d µg/ml | iC3b µg/ml |
|---|---|---|---|---|
| Serum + saline | 296 | 2.4 | 2.83 | 39.82 |
| Serum + de-FCS (10 mg/ml) | 241 | 3.0 | 2.64 | 82.62 |
| Serum + de-FCS (5 mg/ml) | 240 | | | |
| Serum + de-FCS (2.5 mg/ml) | 254 | 2.3 | 2.75 | 32.33 |
| Serum + de-FCS (1.25 mg/ml) | 263 | | | |

As can be seen, there were no major effects on the complement system at any concentration of the de-FCS except for a slight increase in iC3b at the highest concentration. The actual concentration of the de-FCS in the final serum mixture for this sample was 1 mg/ml (9 parts of serum plus 1 part of de-FCS at 10 mg/ml). The effects seen by other experimenters on the inhibition of complement were at concentrations on the order of 1–10 μg/ml.

Serum was mixed with de-FCS, saline, HAGG or Zymosan or combinations thereof, incubated for 30 minutes at 37° C., and examined for effects on CH50 and C4d generation. Proportions of the mixture were 8 parts serum and 2 parts saline+HAGG; or saline+Z, or HAGG+de-FCS, or Z+de-FCS). The de-FCS was at 10 mg/ml. The results are shown in Table III, below.

TABLE III

| Sample | CH50 μg/ml | C4d μg/ml |
| --- | --- | --- |
| Serum + saline | 358 | 3.91 |
| Serum + HAGG | 0 | 41.70 |
| Serum + Z | 59 | 13.37 |
| Serum + HAGG + de-FCS | 0 | 39.17 |
| Serum + Z + de-FCS | 64 | 9.90 |

These results show that defucosylated chondroitin sulfate has little or no effect on complement activation, highlighting the critical nature of the sulfated fucose side-chains for the compound's effect. The doses used were 100–1000 times those tested previously (Wilson et al., J. Immunol, 1984) and there did not appear to be any decrease in the ability of either a classical pathway activator (HAGG) or an alternative pathway activator (Z) to activate complement in the presence of the de-FCS. This can be seen in the absence of change in the CH50 as well as the C4d.

I claim:

1. A method for inhibiting the complement pathway in a mammal comprising administering an effective dose of a composition comprising an active ingredient selected from the group consisting of isolated sea cucumber body wall, isolated sea cucumber epithelial layer, isolated sea cucumber flower, combinations thereof, active derivatives thereof or combinations of active derivatives thereof.

2. The method of claim 1 wherein the active ingredient is administered in an amount per day between about 10 milligrams per kilogram body weight and 1 gram per kilogram body weight.

3. The method of claim 2 wherein the active ingredient is administered in an amount per day of about 25 milligrams per kilogram body weight.

4. The method of claim 1 wherein the composition is in a dosage form suitable for administration orally, rectally, topically or via injection.

5. The method of claim 4 wherein the dosage form is suitable for oral administration.

6. The method of claim 4 wherein the dosage form is suitable for topical administration.

7. The method of claim 4 wherein the dosage form is suitable for administration via injection.

8. The method of claim 1 wherein the active ingredient is an active derivative of isolated sea cucumber body wall, isolated sea cucumber epithelial layer or isolated sea cucumber flower selected from the group consisting of sulfated polysaccharides, sterol glycosides, saponins, lactones, peptides, protamines, glycogens, saccharides, polysaccharides and combinations thereof.

9. The method of claim 8 wherein the active derivative is the sulfated polysaccharide sea cucumber fucosylated chondroitin sulfate.

10. A method for inhibiting the complement pathway in a mammal comprising administering an effective dose of a composition comprising isolated sea cucumber body wall or active derivatives thereof.

11. The method of claim 10 wherein the isolated sea cucumber body wall or active derivative thereof; is administered in an amount per day between about 10 milligrams per kilogram body weight and 1 gram per kilogram body weight.

12. The method of claim 11 wherein the isolated sea cucumber body wall or active derivative thereof is administered in an amount per day of about 25 milligrams per kilogram body weight.

13. The method of claim 10 wherein the composition is in a dosage form suitable for administration orally, rectally, topically or via injection.

14. The method of claim 13 wherein the dosage form is suitable for oral administration.

15. The method of claim 13 wherein the dosage form is suitable for topical administration.

16. The method of claim 13 wherein the dosage form is suitable for injection.

17. The method of claim 10 wherein the active derivative of isolated sea cucumber body wall is selected from the group consisting of sulfated polysaccharides, sterol glycosides, saponins, lactones, peptides, protamines, glycogens, saccharides, polysaccharides and combinations thereof.

18. The method of claim 17 wherein the active derivative is the sulfated polysaccharide sea cucumber fucosylated chondroitin sulfate.

19. A method for inhibiting the complement pathway in a mammal comprising administering an effective dose of a composition comprising isolated sea cucumber epithelial layer or active derivatives thereof.

20. The method of claim 19 wherein the isolated sea cucumber epithelial layer or active derivative thereof is administered in an amount per day between about 10 milligrams per kilogram body weight and 1 gram per kilogram body weight.

21. The method of claim 20 wherein the isolated sea cucumber epithelial layer or active derivative thereof is administered in an amount per day of about 25 milligrams per kilogram body weight.

22. The method of claim 19 wherein the composition is in a dosage form suitable for administration orally, rectally, topically or via injection.

23. The method of claim 22 wherein the dosage form is suitable for oral administration.

24. The method of claim 22 wherein the dosage form is suitable for topical administration.

25. The method of claim 22 wherein the dosage form is suitable for injection.

26. The method of claim 19 wherein the active derivative of isolated sea cucumber epithelial layer is selected from the group consisting of sulfated polysaccharides, sterol glycosides, saponins, lactones, peptides, protamines, glycogens, saccharides, polysaccharides and combinations thereof.

27. The method of claim 26 wherein the active derivative is the sulfated polysaccharide sea cucumber fucosylated chondroitin sulfate.

28. A method for inhibiting the complement pathway in a mammal comprising administering an effective dose of a composition comprising isolated sea cucumber flower or active derivatives thereof.

29. The method of claim 28 wherein the isolated sea cucumber flower or active derivative thereof is administered in an amount per day between about 10 milligrams per kilogram body weight and 1 gram per kilogram body weight.

30. The method of claim 29 wherein the isolated sea cucumber flower or active derivative thereof is administered in an amount per day of about 25 milligrams per kilogram body weight.

31. The method of claim 28 wherein the composition is in a dosage form suitable for administration orally, rectally, topically or via injection.

32. The method of claim 31 wherein the dosage form is suitable for oral administration.

33. The method of claim 31 wherein the dosage form is suitable for topical administration.

34. The method of claim 31 wherein the dosage form is suitable for injection.

35. The method of claim 28 wherein the active derivative of isolated sea cucumber flower is selected from the group consisting of sulfated polysaccharides, sterol glycosides, saponins, lactones, peptides, protamines, glycogens, saccharides, polysaccharides and combinations thereof.

36. The method of claim 35 wherein the active derivative is the sulfated polysaccharide sea cucumber fucosylated chondroitin sulfate.

* * * * *